United States Patent
Akingbade et al.

(10) Patent No.: US 11,684,597 B2
(45) Date of Patent: Jun. 27, 2023

(54) ADMINISTRATION OF TAILORED FEEDSTOCK TO INCREASE NITRO-CONTAINING AMPHENICOL ANTIBIOTIC SUSCEPTIBILITY

(71) Applicant: U.S. Army Research Laboratory, Adelphi, MD (US)

(72) Inventors: Katherine L. Akingbade, Silver Spring, MD (US); Christian J. Sund, Bethesda, MD (US)

(73) Assignee: The United States of America as represented by the Secretary of the Army

( * ) Notice: Subject to any disclaimer, the term of this patent is extended or adjusted under 35 U.S.C. 154(b) by 548 days.

(21) Appl. No.: 16/258,780

(22) Filed: Jan. 28, 2019

(65) Prior Publication Data

US 2020/0237691 A1 Jul. 30, 2020

(51) Int. Cl.
 - *A61K 31/191* (2006.01)
 - *A61K 9/00* (2006.01)
 - *A61K 31/165* (2006.01)
 - *A61K 31/655* (2006.01)

(52) U.S. Cl.
 CPC .......... *A61K 31/191* (2013.01); *A61K 9/0019* (2013.01); *A61K 9/0056* (2013.01); *A61K 31/165* (2013.01); *A61K 31/655* (2013.01)

(58) Field of Classification Search
 CPC .. A61K 31/165; A61K 31/191; A61K 31/655; A61K 9/0019; A61K 9/0056
 See application file for complete search history.

(56) References Cited

U.S. PATENT DOCUMENTS

| 4,371,540 | A | 2/1983 | Lee et al. |
| 8,841,279 | B2 | 9/2014 | Taylor et al. |
| 9,364,467 | B2 | 6/2016 | Golden et al. |
| 2010/0152122 | A1 | 6/2010 | Taylor et al. |
| 2012/0129905 | A1 | 5/2012 | Murakami et al. |
| 2015/0071904 | A1 | 3/2015 | Collins et al. |

FOREIGN PATENT DOCUMENTS

| DE | 102010032590 A1 | | 12/2011 |
| WO | 2008057802 | | 5/2008 |
| WO | WO2016172380 | * | 10/2016 |
| WO | 2017057919 A1 | | 4/2017 |

OTHER PUBLICATIONS

The FDA consumer magazine, 2006, https://www.fda.gov/media/110491/download (Year: 2006).*
Food.r-biopharm (https://food.r-biopharm.com/news/infographic-chloramphenicol/) (Year: 2017).*
Creative Diagnostics (https://www.creative-diagnostics.com/food-analysis/tag-chloramphenicol-54.htm, 2020) (Year: 2020).*
Chloramphenicol (The United States Pharmacopeial Convention, 2007, p. 1-4) (Year: 2007).*
O'Brien et al. (J of General Microbiology, 1971, 67, 265-271) (Year: 1971).*
Servinsky et al. (Microbial Cell Factories, 2014, 13, 139, p. 1-12). (Year: 2014).*
Johnstin et al. (J Biol. Chem, 1935, 110, 279-284). (Year: 1935).*
Sugar Acids, Wikipedia, (https://en.wikipedia.org/wiki/Sugar_acid, 2020). (Year: 2020).*
Wedgewood Pharmacy (Year: 2020).*
ScienceAlert (Year: 2020).*
U.S. Appl. No. 15/939,329, filed Mar. 29, 2018.
Non-Final Office Action issued in U.S. Appl. No. 15/939,329 dated Mar. 27, 2020.
Non-Final Office Action issued in U.S. Appl. No. 15/939,329 dated Apr. 18, 2019.
Final Office Action issued in U.S. Appl. No. 15/939,329 dated Nov. 14, 2019.
"CHLORAMPHENICOL," Purdue Research Foundation, 1996 Available at: http://www.cyto.purdue.edu/cdroms/cyto2/17/chmrx/cap.htm.
Azeza Falghoush, et al., "Osmotic Compounds Enhance Antibiotic Efficacy against Acinetobacter baumannii Biofilm Communities," Appl Environ Microbiol. Oct. 1, 2017; 83(19).
Natalia S.Felix, "Chloramphenicol: Applied Pharmacology," Pediatric Clinics of North America, vol. 3, Issue 2, May 1956, pp. 317-327.
I. W. McLean, Jr., et al., "Susceptibility of Micro-Organisms to Chloramphenicol(CHLOROMYCETIN)" J Clin Invest, 28 (1949), pp. 953-963.
"CHLORAMPHENICOL" webpage, Available at: http://cms.ubqo.com/public/d2595446-ce3c-47ff-9dcc-63167d9f4b80/content/7203f7a7-0831-41c9-ae31-33877efla1e2 (page last updated May 14, 2020).
Drugs.com's "Chloramphenicol Injection" webpage, Available at: https://www.drugs.com/pro/chloramphenicol-injection.html (page last updated Dec. 1, 2019).
Drugs.com's "Inactive Ingredients" webpage. Available at: https://www.drugs.com/inactive/. (Data from sources updated Sep. 30, 2020 or Oct. 1, 2020).
Minimal Inhibitory Concentration Test (MIC). Microchem Laboratory. Available at: http://microchemlab.com/test/minimum-inhibitory-concentration-test-mic. © 2018.
Ken B. Waites, et al., "Standardized Methods and Quality Control Limits for Agar and Broth Microdilution Susceptibility Testing of Mycoplasma pneumoniae, Mycoplasma hominis, and Ureaplasma urealyticum," Journal of Clinical Microbiology, 2020, vol. 50, No. 11, p. 3542-3547.

(Continued)

*Primary Examiner* — Umamaheswari Ramachandran
(74) *Attorney, Agent, or Firm* — Eric B. Compton

(57) ABSTRACT

A method for increasing susceptibility of microorganisms to antibiotics includes providing a microorganism; administering an antibiotic including a nitro-containing amphenicol compound to the microorganism; and administering any of an uronic, aldonic, ulosonic, and aldaric feedstock to the microorganism. The feedstock is adapted to promote cell metabolism, and inhibit antibiotic inactivation pathways in the microorganism causing increased sensitivity of the microorganism to the nitro-containing amphenicol.

17 Claims, 4 Drawing Sheets

(56) References Cited

OTHER PUBLICATIONS

James H. Jorgensen and Mary Jane Ferraro, "Antimicrobial Susceptibility Testing: A Review of General Principles and Contemporary Practices," Medical Microbiology, CID 2009:49, 1749-1755.
Angus C.T. Lo and Kai Man Kam, "Review of Molecular Techniques for Sexually Transmitted Diseases Diagnosis," in Advanced Techniques in Diagnostic Microbiology, 2006, Chap. 22, pp. 353-386.
Non-Final Office Action issued in U.S. Appl. No. 15/939,329 dated Jan. 6, 2021.
David I. Edwards, "Mechanisms of selective toxicity of metronidazole," Br J. Ven Disease 1980; 56, 285-90.

\* cited by examiner

Known Nitro-Containing Amphenicol Antibiotic Compounds

Chloramphenicol

Azidamfenicol

ADMINISTRATION OF TAILORED FEEDSTOCK TO INCREASE NITRO-CONTAINING AMPHENICOL ANTIBIOTIC SUSCEPTIBILITY

GOVERNMENT INTEREST

The embodiments herein may be manufactured, used, and/or licensed by or for the United States Government without the payment of royalties thereon.

This application is related to U.S. patent application Ser. No. 15/939,329 filed Mar. 29, 2018, the disclosure of which is incorporated by reference in its entirety. The '329 application discloses method for increasing susceptibility of microorganisms to antibiotics comprising a nitroimidazole compound. Nitroimidazoles are a class of chemical compounds with active imidazole ring and nitro group at 2'- or 5'-positions. They work mainly on anaerobic bacteria or parasites, and can also be used in tumor treatments.

BACKGROUND

Technical Field

The embodiments herein generally relate to a method for increasing susceptibility of microorganisms to antibiotics, and more particularly, to nitro-containing amphenicol antibiotic compounds.

Description of the Related Art

There are many other families and classes of antibiotics. Amphenicols are broad spectrum antibiotics that can treat aerobic/anaerobic gram positives and gram negatives including and not limited to: *Rickettsia, Chlamyophila, Mycoplasma, Salmonella, Enteracter, Klebsiella, Escherichia, Pseudomonas aeruginosa, Proteus, H. influenzae, Streptococcus pneumoniae* and *Neisseria meningitidis*. They have a phenylpropanoid structure and function by blocking the enzyme peptidyl transferase on the 50S ribosome subunit of bacteria.

While nitroimidazoles are similar to a prodrug, in that, in order for them to be active and act as an antibiotic, they need to be reduced in the cell to an active intermediate. The active intermediate is a free radical and tends to cause DNA breaks and other affects. On the other hand, amphenicols are active as administered. Both nitroimidazole active intermediate and amphenicols are inactivated once they are further reduced.

Over use of these antibiotics has caused a significant increase in antibiotic resistance, resulting in longer hospital stays and increased drug costs. Additionally, use of antibiotics kills the natural gut flora, which can result in intestinal inflammation and possibly fatal diarrhea in children.

Amphenicol antibiotics are typically used as a last resort for multidrug resistant infections due to serious negative side effects. Use of amphenicol has been attributed to bone marrow suppression, aplastic anemia and increased susceptibility to *Clostridium difficile* infections. The annual costs of *C. difficile* treatment is estimated to be $6.3 billion dollars a year and multidrug resistant infections is approximately $2 billion a year, not to mention the cost of treating each infection individually.

Like nitroimidazole antibiotic compounds discussed in the aforementioned '329 application, there are no current methods or additives to increase susceptibility of cells to amphenicol antibiotic compounds unless an additional antibiotic is administered either. Therefore, there is a need to develop a more convenient approach to increase susceptibility of microorganisms to amphenicol antibiotics in fighting infections, thereby reducing side effects associated with antibiotic treatment.

Amphenicol compounds exist including those having nitro- ($-NO_2$) and sulfur oxide- ($-SO_2$) functional groups. This application is specific to the amphenicol compounds containing a nitro- ($-NO_2$) functional group.

SUMMARY

In view of the foregoing, an embodiment herein provides a method for increasing susceptibility of microorganisms to nitro-containing amphenicol antibiotic, the method comprising providing a microorganism; administering an antibiotic comprising a nitro-containing amphenicol compound to the microorganism; and administering any of an uronic, aldonic, ulosonic, and aldaric feedstock to the microorganism, wherein the feedstock is adapted to promote cell metabolism and inhibit antibiotic inactivation pathways in the microorganism causing increased sensitivity of the microorganism to the nitro-containing amphenicol. The nitro-containing amphenicol compound may comprise chloramphenicol or azidamfenicol. The feedstock may comprise a sugar acid or a combination of sugar acids comprising any of an uronic, aldonic, ulosonic, and aldaric acid.

The method may comprise metabolizing galacturonate from the galacturonic acid by producing adenosine triphosphate (ATP) and reduced ferredoxin. The feedstock may be adapted to decrease production of NADH and NADPH in the microorganism. The method may comprise administering the feedstock as a supplement for oral antibiotics. The feedstock may comprise an aqueous solution or a solid form. The method may comprise decontaminating the microorganism. The method may comprise administering the feedstock by intravenous injection, subcutaneous injection, or intraperitoneal injection.

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Embodiments of the present invention provide methods to increase microorganisms' susceptibility to nitro-containing amphenicol antibiotic compounds. As mentioned above, amphenicols have a phenylpropanoid structure and function by blocking the enzyme peptidyl transferase on the 50S ribosome subunit of bacteria. They can treat aerobic/anaerobic gram positives and gram negatives including and not limited to: *Rickettsia, Chlamyophila, Mycoplasma, Salmonella, Enteracter, Klebsiella, Escherichia, Pseudomonas aeruginosa, Proteus, H. influenzae, Streptococcus pneumoniae* and *Neisseria meningitidis*.

FIG. 1 shows the chemical structure for two nitro-containing amphenicol antibiotic compounds: chloramphenicol and azidamfenicol. Chloramphenicol is the common form of nitro-containing amphenicols having an antimicrobial activity and a broad spectrum of action on bacteria including *Staphylococcus aureus, Streptococcus pneumoniae*, and *Escherichia coli*. It is commonly produced synthetically. For treatment, it is typically administered topically, orally, or injected. Azidamfenicol has a similar profile to chloramphenicol. It is typically used topically, such as in eye drops and ointments.

Antibiotics are more effective in cells with active metabolism. Metabolism of the nitro-containing amphenicol compounds in microorganisms may be altered to decrease eukaryotic cytotoxic intermediates (which have been found to result in bone marrow suppression and aplastic anemia) through the selected administration of feedstock as an additive or supplement to control metabolic flux of NADH for decrease metabolic flux through pathways for nitro-containing amphenicol inactivation. For example, intracellular NADH can be decreased through the administration of oxidized feedstock such as galacturonic acid to *Clositridium* sp. By lowering the availability of NADH in a microorganism, there is a decrease in inactivation of the nitro-containing amphenicol which increases its susceptibility in that microorganism. Additionally, this allows bacterial infections to be selectively targeted through the administration of specific feedstocks metabolized only by that species, leaving normal flora alone. This method allows for treatment of infections without the harmful side effects.

The methods for increasing microorganisms' susceptibility to nitro-containing amphenicol antibiotics comprise administering the uronic, aldonic, ulosonic, and/or aldaric substrates or feedstocks. More particularly, the embodiments herein provide for administering effective amount of nitro-containing amphenicol and uronic, aldonic, ulosonic, and/or aldaric substrates or feedstocks to microorganisms.

Particular embodiments use substrates; e.g., uronic, aldonic, ulosonic, and/or aldaric acids or salts that promote cell metabolism but also inhibit or decrease flux through pathways required for antibiotic inactivation and/or repair of antibiotic damage. There may be still some flux, but not as much as with other feedstocks, decreasing the amount of NADH. In particular embodiments, intracellular NADH may be decreased through the administration of oxidized substrates such as galacturonic acid or glucuronic acid to *C. acetobutylicum*. Referring now to the drawings, and more particularly to FIGS. 2 through 4, where similar reference characters denote corresponding features consistently throughout the figures, there are shown preferred embodiments.

"Antibiotics" as used herein refers to drug used in the treatment and prevention of bacterial infections, or any substance used against microbes.

"Microorganism" as used herein refers to unicellular or mutlicellular organisms, includes bacteria, archaea, protists, protozaons, or eukaryotes; e.g., human, animal, and plant cells.

"Anaerobic organism" as used herein refers to any organism that may not or must not require oxygen for growth, organism may be unicellular or multicellular organism.

"Feedstock" and "Substrate" may be used interchangeably and is defined as material comprising carbohydrate or sugar (e.g. glucose, gluconate, and galacturonate).

"Effective amount" is used herein to denote a quantity or concentration of that antibiotics and/or substrate is known to be effective to achieve the desired and known result of the antibiotics and/or substrate. The actual amount contained in the molecular complex or composition, likely will vary since some of the antibiotics and/or substrate composition may not completely penetrate the microorganism together. Using the guidelines provided herein, those skilled in the art are capable of determining the acceptable amount of antibiotics and substrate described herein, and to use the requisite amount. For example, a suitable dosage adjustment may be made by the attending physician or veterinarian depending upon the age, sex, weight and general health of the subject. Such a composition may be administered parenterally, optionally intramuscularly or subcutaneously. However, the composition may also be formulated to be administered by any other suitable route, including orally or topically.

In another embodiment, the nitro-containing amphenicol compound of the composition may include, but are not limited to, compounds such as chloramphenicol and azidamfenicol.

A common carbohydrate such as glucose a type of aldose, is oxidized at carbon one position from aldehyde to carboxyl group, the product is called aldonic acid, or more specifically gluconic acid. The aldonic acid usually has multiple hydroxyl groups. The general chemical formula is $HOOC—(CHOH)_n—CH_2OH$. Oxidation of the terminal hydroxyl group occurs instead of the terminal aldehyde and yields a uronic acid, while oxidation of both terminal ends yields an aldaric acid. Aldonic acid may exist as stereoisomers as D, L, and DL or R, S and RS forms. Hence D-glucose is oxidized to D-gluconic acid and D-gluconolactone.

In one embodiment, any of the uronic, aldonic, ulosonic, and aldaric feedstock may be an aqueous solution or solid form. Thus, for example it may be in tablet, coated tablet, delayed or sustained release coated tablet, capsule, suppository, pessary, gel, emulsion, syrup, dispersion, suspension, emulsion, powder, cream, paste, etc.

In another embodiment, any of the uronic, aldonic, ulosonic, and aldaric feedstock may be administered as a supplement for oral antibiotics, such as an antibiotic chaser in a shake or drink form.

In one embodiment, any of the uronic, aldonic, ulosonic, and aldaric feedstock may be administered with two or more different therapeutic compounds; e.g., with two different antibiotics. Two different antibiotics with substrates may be administered either in the same formulation or in a separate formulation, either concomitantly or sequentially.

Antibiotics against anaerobes microorganisms include penicillin G, amphenicol, imipenem, ampicillin-sulbactam, clindamycin, cefoxitin, piperacillin, ceftizoxime, cefoperazone, erythromycin, moxalactam, cefotetan, cefipime or a combination of antibiotics.

In one embodiment, nitro-containing amphenicol; e.g., chloramphenicol, is effective for the treatment of anaerobic infections, such as intra-abdominal infections, gynecologic infections, septicemia, endocarditis, bone and joint infections, central nervous system infections, respiratory tract infections, skin and skin-structure infections, and oral and dental infections.

In another embodiment, nitro-containing amphenicol and any of the uronic, aldonic, ulosonic, and aldaric feedstock may be used with other antibiotics for treatment of mixed aerobic and anaerobic infection, or in combination with other antibacterial agents that are appropriate for the treatment of the aerobic infection, or other anaerobic infections.

The composition of the embodiments herein may be administered to any part, organ, interstice or cavity of a human or non-human body that is subject to an infection or radiation. For example, the composition may be administered by, but not limited to, oral and non-oral preparations (e.g., intramuscular, subcutaneous, transdermal, visceral, IV (intravenous), IP (intraperitoneal), intraarticular, placement in the ear, ICV (intracerebralventricular), intraarterial, intrathecal, intracapsular, intraorbital, injectable, pulmonary, nasal, rectal, and uterine-transmucosal preparations).

In some embodiments, a process of decontaminating the surface occurs by applying the feedstock or substrate with antibiotics to a surface that is contaminated with one or more microbes. Any delivery mechanism for decontaminating a surface may be used including spraying, immersing, or other contact mechanism.

Figure 1:
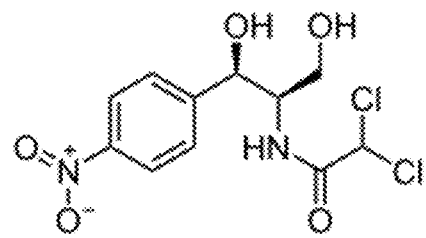
FIG. 1 shows the chemical structures of two known nitro-containing amphenicol antibiotic compounds: chloramphenicol and azidamfenicol.
Figure 1:
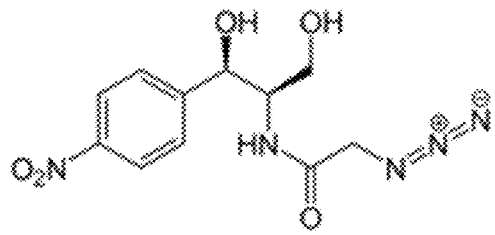
Figure 2:
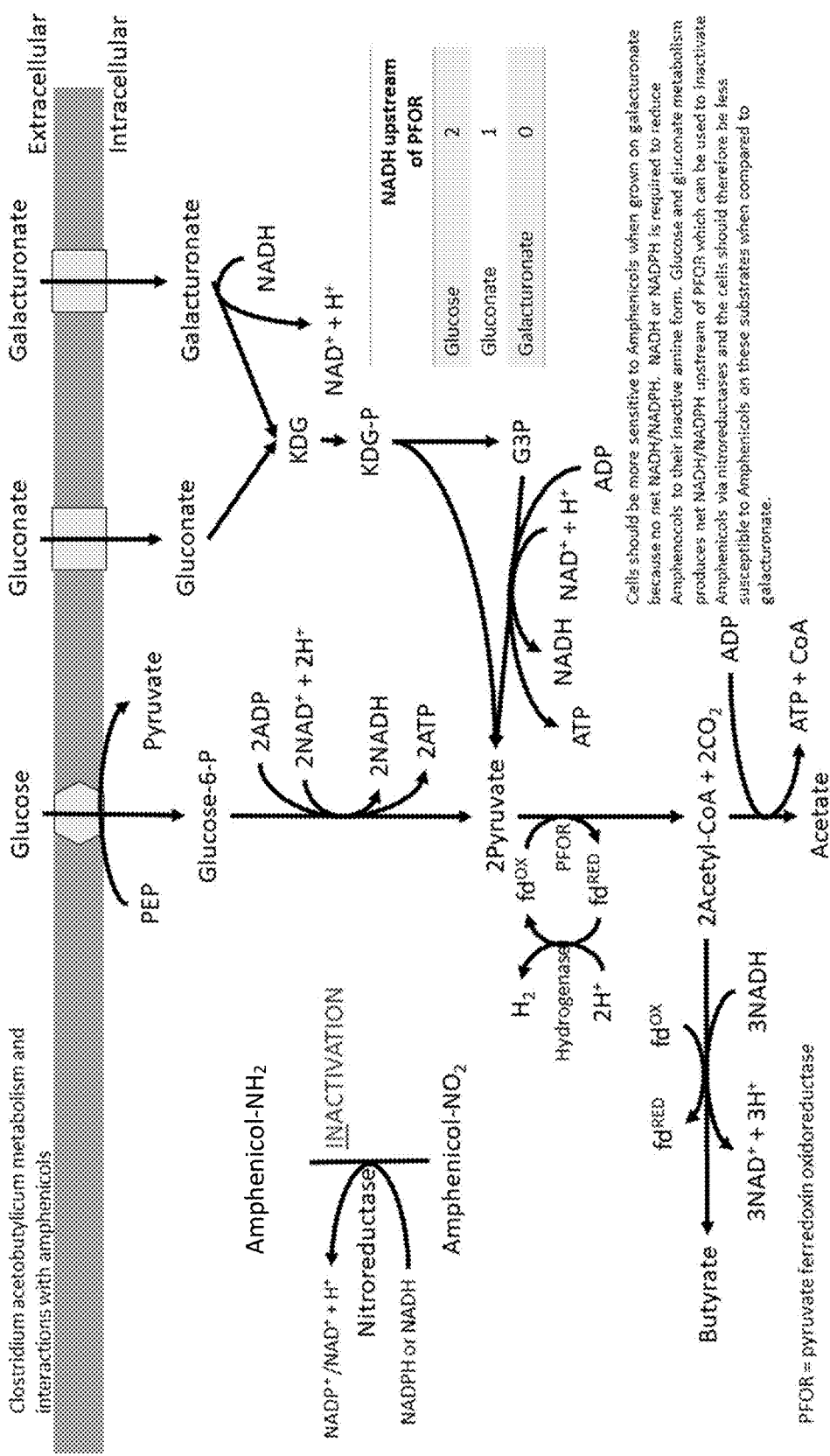
FIG. 2 is a schematic illustrating *C. acetobutylicum* metabolism and interactions with a nitro-containing amphenicol compound.
Figure 3:
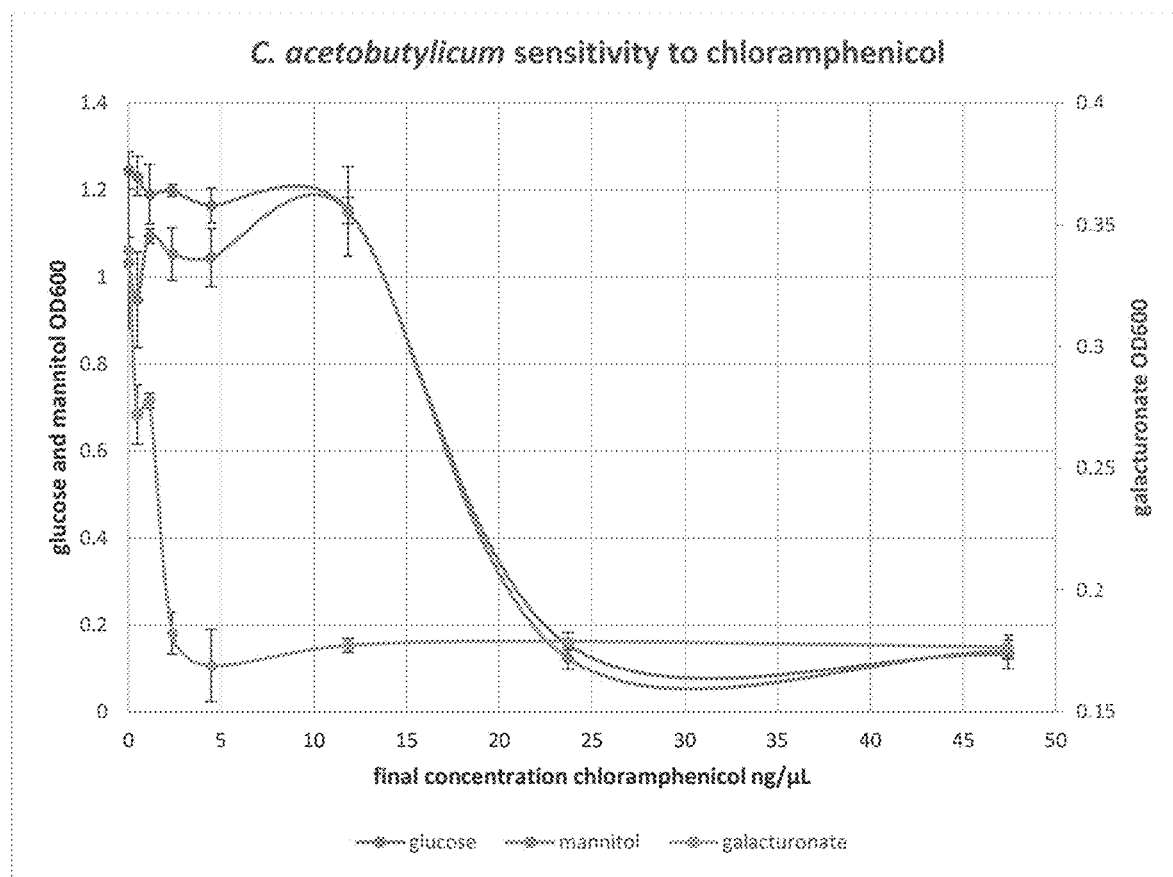
FIG. 3 is a graph illustrating *C. acetobutylicum* sensitivity to chloramphenicol after 24 hours.
Figure 4:
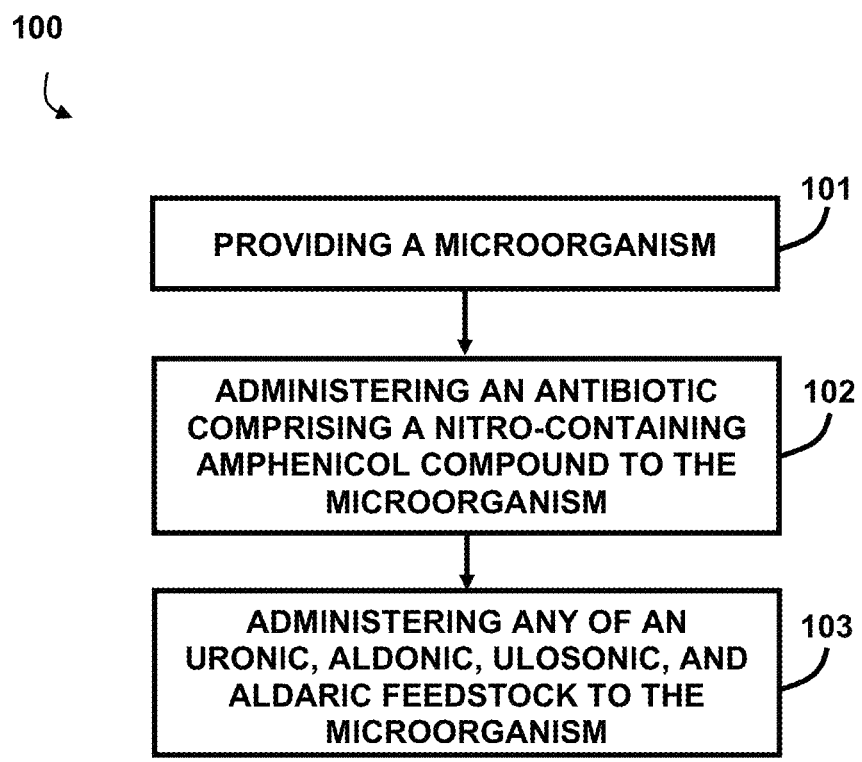
FIG. 4 is a flow diagram illustrating a method of administering a nitro-containing amphenicol compound to a microorganism.

FIG. 2 illustrates *C. acetobutylicum* metabolism and interactions with a nitro-containing amphenicol compound with respect to three feedstocks: glucose, gluconate, and galacturonate. Conversion of galacturonate, and glucose to acetyl-CoA produces similar amounts of ATP and reduced ferredoxin to help drive metabolism and nitro-containing amphenicol inactivation. Further, conversion of galacturonate and glucose to acetyl-CoA produces different amounts of NADH.

More particularly, FIG. 2 shows how three feedstocks (i.e., glucose, gluconate, and galacturonate) are assimilated into central metabolism of the *C. acetobutylicum*. The feedstocks may in the form of substrates as conventionally used in in vitro experiments, for instance. All three feedstocks produce two moles of pyruvate per mole of the feedstock compound and the pyruvate is converted to acetyl-CoA and $CO_2$ by pyruvate ferredoxin oxidoreductase (PFOR). PFOR, the hydrogenase, and reduced ferredoxin have all been shown to inactivate nitro-containing amphenicols. On a molar basis, all three feedstocks produce equivalent amounts of reduced ferredoxin and metabolize equivalent levels of pyruvate via PFOR. The feedstocks differ in the amount of NADH that is produced as shown in Table 1 below. Per mole of glucose the cells produce 2 moles of NADH upstream of pyruvate while during growth on galacturonate there is no net NADH production. The lack of NADH production reduces the capacity of the organism to inactivate the nitro-containing amphenicols via nitroreductases or other related enzymes.

TABLE 1

NADH/NADPH Production

| Substrate | NADH/NADPH produced upstream of PFOR |
|---|---|
| glucose | 2 |
| gluconate | 1 |
| galacturonate | 0 |

Experimental evidence suggests microorganism (e.g., cells) should be more sensitive to nitro-containing amphenicols when grown on galacturonate because there is no net NADH/NADPH produced. NADH and NADPH are required to reduce amphenicols to their inactive form. Glucose and nitro-containing amphenicols metabolism produces net NADH/NADPH upstream of PFOR which can be used to inactivate those amphenicols via nitroreductases and the cells should therefore be less susceptible to those amphenicols on these substrates when compared to galacturonate.

The feeding strategy provided by the embodiments herein and described in FIG. 2 may be utilized for a broad range of anaerobic organisms due to evolutionary conservation of the pathway for galacturonate metabolism and the need to reduce the substrate for entry into glycolysis. Depending on the target organism other feeding strategies, such as use of different aldonic and uronic acid carbohydrates, may be used to meet the criteria of providing ATP and reduced ferredoxin while minimizing the production of NADH/NADPH. Accordingly, by decreasing the breakdown of the intermediates by the cells, the sensitivity increases.

The two main sources of reduced electron carriers in *C. acetobutylicum* are NADH from lower glycolysis and reduced ferredoxin from PFOR. Electron carriers are reoxidized by the hydrogenase, which couples ferredoxin oxidation with proton reduction, and by reductive conversion of acetyl-CoA to butyrate. Cells gain one ATP per acetyl-CoA by conversion to acetate, as opposed to 0.5 ATP per acetyl-CoA generated during reduction to butyrate. It is therefore more favorable from the standpoint of ATP yield to use the hydrogenase to reoxidize electron carriers. Electrons may be shuffled between NADH and ferredoxin by the NADH-ferredoxin oxidoreductase or butyryl-CoA dehydrogenase, thus it is possible for reducing equivalents formed in lower glycolysis to be oxidized indirectly via the hydrogenase.

Unlike nitroimidazole antibiotic compounds which require activating by the cells, nitro-containing amphenicols antibiotic compounds do not. That is because amphenicols are a class of antibiotics with a phenylpropanoid structure which functions by blocking the enzyme peptidyl transferase on the 50S ribosome subunit of bacteria. The drug can be inactivated by a reduction step. On the other hand, nitroimidazoles have nonspecific action and thus needs to be activated once inside the bacteria cell through a reduction to an intermediate that has a free radical. The free radical on the chemical causes DNA damage and other damage. The intermediate is inactivated through further reduction.

Inactivation of nitro-containing amphenicols can occur through several different mechanisms. The bacteria reduce nitro groups (—$NO_2$) to an amine (—$NH_2$). This process requires nitroreductases or other redox enzymes to reduce the nitro groups while oxidizing intracellular electron carriers such as NADH, NADPH, thioredoxin, flavodoxin, rubredoxin, etc. The nitro-containing amphenicol compound leads to inhibition of protein expression which is repaired by the reversible binding of the antibiotic to the ribosome. Thus, when the microorganism (e.g. cells) are fed nitro-containing amphenicol compounds, the result is decreased production of NADH and NADPH, which in turn causes a reversal in ferredoxin oxidation/reduction cycle via the hydrogenase towards oxidized ferredoxin. As a result, the cells are metabolically active, but have diminished capacity to reduce nitro-containing amphenicol to their inactive form and a diminished capacity to express proteins. The toxic intermediates formed from the reduction and inactivation of the antibiotic have been known to possibly cause severe side effects such as bone marrow suppression and aplastic anemia.

The combined effect is that bacterial cells have increased sensitivity to chloramphenicol and in turn diminishes the formation of eukaryotic cytotoxic intermediates of the antibiotic (resulting in bone marrow suppression and aplastic anemia).

In another embodiment, administering oxidized feedstock to *C. acetobutylicum*, antibiotic susceptibility increases at least one and a half fold or greater compared to administering glucose as a feedstock.

In another embodiment, the different components of the feedstocks may be packaged together with antibiotics or in separate containers. If appropriate, and mixed immediately before use, such packaging of the components separately may permit long-term storage without losing the active component's function. Sterilization may be preceded or followed by packing into containers. If desired, the composition of the embodiments herein may contain pharmaceutically acceptable additives, such as dissolving aids, buffering components, stabilizers, and the like. The antibiotics and/or substrates may be supplied in containers of any sort such at the life of the different components are preserved and are not adsorbed or altered by the materials of the container. For example, sealed glass ampules may contain lyophilized substrates and variants, derivatives and structural equivalents thereof, or buffers that have been packaged under a neutral, non-reacting gas, such as nitrogen. Other containers include test tubes, vials, flasks, bottles, syringes, or the like. Containers may have a sterile access port, such as a bottle having a stopper that may be pierced by a hypodermic injection needle. Other containers may have two compartments that are separated by a readily removable membrane that upon removal permits the components to be mixed. Removable membranes may be glass, plastic, rubber, etc.

Suitable pharmaceutically acceptable carriers facilitate administration of the antibiotic and substrate or feedstocks are physiologically inert and/or nonharmful. Carriers may be selected by one skilled in the art. Exemplary carriers include sterile water or saline, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations may be used.

The substrates or feedstock with or without antibiotic provided by the embodiments herein may additionally contain stabilizers such as thimerosal (ethyl(2-mercaptobenzoate-S)mercury sodium salt) (available from Sigma Chemical Company, St. Louis, Mo.), for example, or physiologically acceptable preservatives.

The composition provided by the embodiments herein may also contain conventional pharmaceutical ingredients, such as preservatives, or chemical stabilizers. Suitable ingredients operable herein include, for example, casamino acids, gelatin, phenol red, N—Z amine, monopotassium diphosphate, lactalbumin hydrolysate, and dried milk.

The nitro-containing amphenicol may be formulated into a composition in a free base, neutral or salt form. Pharmaceutically acceptable salts include the salts formed with a free carboxyl group or amine group derived from inorganic bases such as for example, sodium, potassium, ammonium, calcium or ferric hydroxides; or such organic bases as isopropylamine, trimethylamine, histidine or procaine. The antibiotics and/or substrates may be stable under the conditions of manufacture and storage, and preserved against the contaminating action of microorganisms. It will be appreciated that endotoxin contamination should be kept minimally at a safe level.

Bacterial culture conditions and strains have been previously published. All strains and cultures were maintained or grown in in an atmosphere of 5.0% $H_2$, 5.0% $CO_2$, and 90.0% $N_2$. *Clostridium acetobutylicum* strain ATCC 824 was obtained from ATCC and cultured using company protocol at 37° C. into Clostridial growth medium or CGM containing 0.75 g $KH_2PO_4$, 0.75 g $K_2HPO_4$, 1.0 g NaCl, 0.017 g $MnSO_4.5H_2O$, 0.70 g $MgSO_4.7H_2O$, 0.01 g $FeSO_4.7H_2O$, 2.0 g 1-asparagine, 5.0 g yeast extract, 2.0 g $(NH_4)_2SO_4$, and 0.5% final concentration of desired carbohydrate—D-glucose, D-galacturonic acid, D-gluconic acid—at pH 6.5. Active cultures from initial growth stock were added to potato glucose medium to be maintained and stored as a spore solution. Potato glucose medium or PGM contains per liter of $H_2O$—150 g grated fresh potato, 10 g D-glucose, 0.5 g $(NH_4)SO_4$, and 3 g $CaCO_3$. The medium was boiled for 1 hour and strained through gauze before sterilization and use for culture. Spore solution was activated for culturing through a heat shock at 80° C. for 9 minutes. Shocked spore solution was added to CGM containing the feed stock of choice and grown to late log of 0.8 at optical density of 600 nm ($OD_{600}$) at 37° C. Theses cultures were then used to perform antibiotic sensitivity experiments.

The protocol for antibiotic sensitivity test was performed as follows in anaerobic conditions: 200 μL of CGM medium containing either 0.5% D-galacturonate or D-glucose was aliquoted into a sterile Costar® 96-well polystyrene flat bottom plate in triplicate per test condition. Chloroamphenicol was dissolved in ethanol at different concentrations. Each chloroamphenicol concentration was added to each well in triplicate and considered a test condition. Test conditions included addition of 1 μL of ethanol, 1 of sterile water, 1 μL 0.1 mg $mL^{-1}$, 1 μL 0.25 mg $mL^{-1}$, 1 μL 0.5 mg $mL^{-1}$, 1 μL 1 mg $mL^{-1}$, 1 μL 2.5 mg $mL^{-1}$, 1 μL 5 mg $mL^{-1}$, 1 μL 10 mg $mL^{-1}$, 1 μL 20 mg $mL^{-1}$, and 1 μL 10 mg $mL^{-1}$. 10 μL of $OD_{600}$ 0.8 *Clostridium acetobutylicum* culture grown in CGM containing 0.5% D-galacturonate was aliquoted into each test condition containing D-galacturonic acid. 10 of $OD_{600}$ 0.8 *Clostridium acetobutylicum* culture grown in CGM containing 0.5% D-glucose was aliquoted into each test condition containing D-glucose. The final concentrations of amphenicol after addition of culture are as follows 0.0 μg $mL^{-1}$, 0.0 μg $mL^{-1}$, 0.47 μg $mL^{-1}$, 1.18 μg $mL^{-1}$, 2.37 μg $mL^{-1}$, 4.74 μg $mL^{-1}$, 11.85 μg $mL^{-1}$, 23.7 μg $mL^{-1}$, 47.4 μg $mL^{-1}$, 94.8 μg $mL^{-1}$, 142.0 μg $mL^{-1}$. The 96-well plate was covered and incubated for 20 hours at 37° C. The optical density of the cultures in the wells were measured at 600 nm via a commercially available plate reader.

As illustrated in FIG. 3, administering oxidized feedstock to *C. acetobutylicum*, antibiotic (chloraamphenicol) susceptibility increases during growth on galacturonate when compared to growth on glucose. Galacturonate and gluconate produce similar amounts of ATP and reduced ferredoxin when compared to glucose to help drive metabolism. Metabolism of gluconate and galacturonate results in less production of NADH/NADPH when compared to growth on glucose which impairs chloramphenicol inactivation and repair of oxidative damage. In vitro experiments show that administering oxidized feed stock to anaerobic bacteria, C. acetobutylicum, antibiotic susceptibility increases 10 fold compared to administering glucose as a feed stock. The MIC for galacturonic acid for final concentration of chloramphenicol is 2.4 ng/μL and for glucose is 23.7 ng/μL after 24 h of growth. This experiment has been perform several times and was based off of the proposed model.

FIG. 4 is a flow diagram illustrating a method 100 for increasing susceptibility of microorganisms to nitro-containing amphenicol antibiotics, according to an embodiment herein. The method 100 comprises providing (101) a microorganism; administering (102) an antibiotic comprising a nitro-containing amphenicol compound to the microorganism; and administering (103) any of an uronic, aldonic, ulosonic, and aldaric feedstock to the microorganism, wherein the feedstock is adapted to promote cell metabolism and inhibit antibiotic inactivation pathways in the microorganism causing increased sensitivity of the microorganism to the nitro-containing amphenicol. In one example, the administering processes (102) and (103) may be sequential. In another example, the administering processes (102) and (103) may be simultaneous. The nitro-containing amphenicol compound may comprise chloramphenicol or azidamfenicol. The feedstock may comprise a sugar acid or a combination of sugar acids comprising any of an uronic, aldonic, ulosonic, and aldaric acid.

The method may comprise metabolizing gluconate from the glucuronic acid by producing adenosine triphosphate (ATP) and reduced ferredoxin. The feedstock may be adapted to decrease production of NADH and NADPH in the microorganism. The method may comprise administering the feedstock as a supplement for oral antibiotics. The feedstock may comprise an aqueous solution or a solid form. The method may comprise decontaminating the microorganism. The method may comprise administering the feedstock by intravenous injection, subcutaneous injection, or intraperitoneal injection.

The embodiments herein decrease the concentration of nitro-containing amphenicol antibiotic required for treatment through the use of naturally occurring feedstocks. The embodiments herein increase the susceptibility of the targeted cells to nitro-containing amphenicols, without requiring an additional antibiotic to be administered. By utilizing specific naturally occurring feedstocks as compared to synthetic chemicals or additional antibiotics, the embodiments herein decrease the chance of possible side effects to the patient and decrease the cost of production.

Furthermore, the embodiments herein decrease the concentration of the nitro-containing amphenicol antibiotic required for treatment by targeting specific cells for susceptibility as compared to natural flora. Targeting occurs because not all bacteria can grow on the same feedstock and there for can be tailored for bacteria of interest. This may decrease antibiotic production costs and possible patient side effects (e.g., diarrhea, intestinal inflammation, liver damage, etc.). Additionally, by controlling the cells NADH production, the embodiments herein may decrease antibiotic resistance through the inhibition of antibiotic breakdown which requires energy input.

The embodiments herein may be used in various capacities, including as a treatment for numerous types of infections, control of microbiomes to support health and improve performance, as well as for decontamination of biohazardous environments. Additionally, the tailored feedstock used by the embodiments herein may be used as an additive to suppositories, topical creams and ointments, eye drops, injections, and liquid oral antibiotics emulsions. The tailored feedstock may be administered as a supplement for oral antibiotics such as an "antibiotic chaser" in a shake form or drink form, in various examples. Additionally, the tailored feedstock may be made as a shake or additive to a diet plan for meals prepared for the patient to support antibiotic susceptibility.

Furthermore, the embodiments herein may be used as a feedstock to make the bacterial infection more susceptible to nitro-containing amphenicols through the control of the metabolic flux of NADH/NADPH by acting as an active ingredient to reduce antibiotic inactivation. The method provided by the embodiments herein offers a unique solution in that it may be used as a feedstock and active ingredient and not an additive for hydration/moisturizing and/or as part of a salt for the antibiotic as a PPI to help deal with the pH in the patient's stomach.

The embodiments herein increase the nitro-containing amphenicol antibiotic sensitivity by feeding cells (e.g., microorganisms, multicellular organisms) substrates that promote metabolism but inhibit pathways required for antibiotic inactivation and/or repair of antibiotic damage.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

What is claimed is:

1. A method for increasing susceptibility of microorganisms to antibiotics, the method comprising:

providing a microorganism;

administering an antibiotic composition comprising a nitro-containing amphenicol compound to the microorganism, wherein the microorganism is susceptible to the nitro-containing amphenicol compound; and administering a feedstock comprising a sugar acid selected from the group consisting of an uronic, aldonic, ulosonic, and aldaric, or any salt thereof to the microorganism, wherein the feedstock is adapted to promote cell metabolism and inhibit antibiotic inactivation pathways in the microorganism causing increased sensitivity of the microorganism to the nitro-containing amphenicol.

2. The method of claim 1, wherein the nitro-containing amphenicol compound is selected from the group consisting of chloramphenicol and azidamfenicol.

3. The method of claim 1, wherein the feedstock comprises a sugar acid or a combination of sugar acids comprising two or more of uronic, aldonic, ulosonic, and aldaric acid, or any salt thereof.

4. The method of claim 3, wherein the microorganism metabolizes galacturonate from galacturonic acid by producing adenosine triphosphate (ATP) and reduced ferredoxin.

5. The method of claim 1, wherein the feedstock is adapted to decrease production of NADH and NADPH in the microorganism.

6. The method of claim 1, comprising administering the feedstock as a supplement for oral antibiotics.

7. The method of claim 1, wherein the feedstock comprises an aqueous solution or a solid form.

8. The method of claim 1, comprising administering the feedstock by intravenous injection, subcutaneous injection, or intraperitoneal injection.

9. A method for increasing susceptibility of microorganisms to antibiotics, the method comprising:
   administering an antibiotic comprising a nitro-containing amphenicol compound to a microorganism, wherein the microorganism is susceptible to the nitro-containing amphenicol compound;
   administering a feedstock comprising a sugar acid selected from the group consisting of uronic, aldonic, ulosonic, and aldaric, or any salt thereof to the microorganism,
   wherein the feedstock is adapted to promote cell metabolism and inhibit antibiotic inactivation pathways in the microorganism causing increased sensitivity of the microorganism to the nitro-containing amphenicol.

10. An antibiotic composition comprising:
    a nitro-containing amphenicol compound selected from the group consisting of chloramphenicol and azidamfenicol; and
    a feedstock comprising a sugar acid selected from the group consisting of an uronic, aldonic, ulosonic, and aldaric, or any salt thereof,
    wherein the feedstock is adapted to promote cell metabolism and inhibit antibiotic inactivation pathways in the microorganism causing increased sensitivity of the microorganism to the nitro-containing amphenicol.

11. The antibiotic composition of claim 10, further comprising a carrier selected from the group consisting of: sterile water, saline, calcium phosphate, gelatin, dextran, agar, pectin, peanut oil, olive oil, sesame oil, water, glycerol monostearate, glycerol distearate, wax, and polymer.

12. The antibiotic composition of claim 10, further comprising a stabilizer.

13. The antibiotic composition of claim 12, wherein the stabilizer comprises thimerosal.

14. The antibiotic composition of claim 10, further comprising: a preservative or chemical stabilizer selected from the group consisting of: casamino acids, gelatin, phenol red, N-Z amine, monopotassium diphosphate, lactalbumin hydrolysate, and dried milk.

15. The antibiotic composition of claim 10, wherein said nitro-containing amphenicol compound is in a free base, neutral or salt form.

16. The antibiotic composition of claim 15, wherein said salt form of the nitro-containing amphenicol compound is selected from a free carboxyl group or amine group derived from an inorganic or organic base.

17. The antibiotic composition of claim 10, wherein said composition is an aqueous solution or solid form.

* * * * *